United States Patent [19]

Nudelman

[11] Patent Number: 5,798,386
[45] Date of Patent: Aug. 25, 1998

[54] ANGIOGENIC LIPID FORMULATIONS

[75] Inventor: Edward D. Nudelman, Seattle, Wash.

[73] Assignee: Cell Therapeutics, Inc., Seattle, Wash.

[21] Appl. No.: 611,980

[22] Filed: Mar. 4, 1996

Related U.S. Application Data

[63] Continuation-in-part of Ser. No. 285,153, Aug. 3, 1994, abandoned.

[51] Int. Cl.$^6$ .................... A01N 37/02; A01N 37/06
[52] U.S. Cl. .................. 514/547; 514/549; 514/723; 554/223; 554/227
[58] Field of Search .................... 554/223, 227; 514/547, 549, 723

[56] References Cited

U.S. PATENT DOCUMENTS

| | | |
|---|---|---|
| 3,294,639 | 12/1966 | Chalmers et al. . |
| 3,298,906 | 1/1967 | Knowles . |
| 3,432,602 | 3/1969 | Brohult et al. . |
| 3,659,022 | 4/1972 | Youngdale et al. . |
| 3,888,994 | 6/1975 | Wagner et al. . |
| 3,952,107 | 4/1976 | Shibata . |
| 3,978,092 | 8/1976 | Ichikawa et al. . |
| 4,016,212 | 4/1977 | Leimgruber et al. . |
| 4,046,914 | 9/1977 | Hallgren et al. . |
| 4,126,702 | 11/1978 | Vanderberghe et al. . |
| 4,871,768 | 10/1989 | Bistrian et al. . |
| 4,874,795 | 10/1989 | Yesair . |
| 4,897,263 | 1/1990 | Hunter . |
| 4,943,560 | 7/1990 | Wigness et al. ............. 514/11 |
| 5,011,680 | 4/1991 | Suzuki et al. . |
| 5,095,154 | 3/1992 | Liu . |
| 5,173,511 | 12/1992 | Brohult et al. . |
| 5,183,811 | 2/1993 | Masaki et al. . |
| 5,227,533 | 7/1993 | Plotkin et al. . |
| 5,243,089 | 9/1993 | Plotkin et al. . |
| 5,352,440 | 10/1994 | Gilchrest et al. . |
| 5,358,714 | 10/1994 | Green . |
| 5,403,833 | 4/1995 | Calne ......................... 514/171 |
| 5,434,182 | 7/1995 | Issacs et al. . |
| 5,569,462 | 10/1996 | Martinson et al. ............. 424/424 |

FOREIGN PATENT DOCUMENTS

WO 96/03981  2/1996  WIPO .

OTHER PUBLICATIONS

Chem Abs 67: 508166 Slotboom et al "Chemistry and Physics of Lipids" (1967) 1(3) 192–208.

Chem Abs 67:116521 Serebryakova et al Zh. Org. Khim 3(8) 1412–15 (1967).

Foglia et al., *Lipids*, vol. 23, No. 5, pp. 430–434, "Oxidation of 1–O–(Alk–1–enyl)–2,3–Di–O–Acylglycerols: Models for Plasmalogen Oxidation", 1988.

Ford et al., *American Physiological Society*, vol. 258, pp. C30–C36, "Activation of myocardial protein kinase C by plasmalogenic diglycerides", 1990.

Ford et al., *J. Biol. Chem.*, vol. 264, No. 23, Issue of Aug. 16, pp. 13818–13824, "Activation of Protein Kinase C by Naturally Occuring Ether–linked Diglycerides", 1989.

Gigg, R., *Ether Lipids: Chemistry and Biology*, Ed. By Fred Snyder, Chapter V, pp. 87–108, "The Chemical Synthesis of Plasmalogens", 1972.

Hallgren et al., *Chemical Abstracts*, vol. 80, No. 120255k, p. 382, "Therapeutic substituted alkyl or alkenyl glyceryl ethers", 1974.

Hanahan, D., *Etherlipids: Chemistry and Biology*, Ed. By Fred Snyder, Chapter II, pp. 25–29, "Ether–linked lipids: Chemistry and Methods of Measurement", 1972.

Knorr et al., *J. Chromatography*, vol. 526, pp. 303–318, "Simple method for the analysis of glycerol enol ethers derived from plasmalogens in complex lipid mixtures and subsequent determination of the aldehydic components by gas chromatography–mass spectrometry", 1990.

Lin et al., *Lipids*, vol. 12, No. 7, pp. 620–625, "Composition of O–Alkyl and O–Alk–1–enyl Moieties in the Glycerolipids of the Human Adrenal", 1977.

Seher et al., *Thermal Analysis*, vol. 3, Proceedings Third ICTA DAVOS, pp. 109–119, "Characterization of Unusual Lipids by Novel Thermoanalytical Techniques", 1971.

Snyder et al., *Cancer Res.*, vol. 28, pp. 972–978, "The Occurrence and Metabolism of Alyl and Alk–1–enyl Ethers of Glycerol in Transplantable Rat and Mouse Tumors", 1968.

Snyder et al., *Cancer Res.*, vol. 29, pp. 251–257, "Alkyl and Alk–1–enyl Ethers of Glycerol in Lipids from Normal and Neoplastic Human Tissues", 1969.

Su et al., *Lipids*, vol. 9, No. 3, pp. 208–213, "On the Levels of Alkyl and Alk–1–enyl Glycerolipids in Normal and Neoplastic Tissues: A Method of Quantification", 1974.

Touabi et. al., *Biochim. Biophys. Acta*, vol. 202, pp. 486–495, "Lipolysis and Potassium Accumulation in Isolated Fat Cells Effect of Insulin and Lipolytic Agents", 1970.

Blank et al., *Chemical Abstracts*, vol. 82, No. 151647k, p. 238, "Method for the quantitative determination of glycerolipids containing O–alkyl and O–alk–1–enyl moieties", 1975.

Baumann et al., *Chemical Abstracts*, vol. 70, No. 46750t, p. 261, "1–Alkenyl ethers of glycerol and ethanediol", 1969.

Baumann et al., *Chemical Abstracts*, vol. 73, No. 41867p, p. 261, "Alkoxylipids. VI. Molecular structures of the neutral alkoxylipids of ratfish liver", 1970.

(List continued on next page.)

*Primary Examiner*—Herbert J. Lilling
*Attorney, Agent, or Firm*—Stephen Faciszewski; Cynthia L. Shumate

[57] ABSTRACT

There is disclosed an aqueous formulation for vascularizing ischemic or grafted tissue, comprising an alk-1-enyl glycerol derivative having the formula:

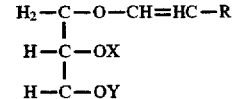

wherein R is a straight or branched $C_{1-24}$ saturated or unsaturated alkyl or a straight or branched $C_{1-24}$ aryl and X and Y each is H or an saturated or unsaturated alkyl group having from 2 to 26 carbon atoms, or a monoglyceride having a $C_{1-24}$ ether-linked saturated alkyl in an aqueous buffered pharmaceutical carrier.

10 Claims, 2 Drawing Sheets

OTHER PUBLICATIONS

Chalmers et al., *Chemical Abstracts*, vol. 67, No. 81324s, p. 7651, "Isolation of α-glyceryl ethers from marine oils", 1967.

Chernaya et al., *Chemical Abstracts*, vol. 82, No. 18681a, p. 116, "Synthesis and study of alkyl ethers", 1975.

Gilbertson et al., *Chemical Abstracts*, vol. 63, No. 9445, "Nonphosphatide fatty acyl esters of alkenyl and alkyl ethers of glycerol", 1963.

Hammond et al., *Plast. Reconst. Surg.*, vol. 91, pp. 316–321, "The Dorsal Skin–Flap Model in the Rat: Factors Influencing Survival," 1993.

Hanahan, *Chemical Abstracts*, vol. 77, No. 164991q, p. 446, "Ether–linked lipids. Chemistry and methods of measurement", 1972.

Hayashi et al., *Chemical Abstracts*, vol. 89, No. 212271b, p. 339, "The lipids of marine animals from various habitat depths. VII. Compositions of diacyl glyceryl ethers in the flesh lipids of two deep–sea teleost fish, Seriollela sp. and S. Punctata", 1978.

Snyder, et al., *Chemical Abstracts*, vol. 69, No. 1348f, p. 128, "The occurrence and metabolism of alkyl and alk—1–enyl ethers of glycerol in transplantable rat and mouse tumors", 1968.

Su, et al., *Chemical Abstracts*, vol. 81, No. 22741S, p. 199, "Levels of alkyl and alk–1–enyl glycerolipids in normal and neoplastic tissues. Methods of Quantification", 1974.

Titov et al., *Chemical Abstracts*, vol. 80, No. 120253h, p. 382, "cis–1–Alkenyl ethers of glycerol", 1974.

Vedder et al., *Plast. Reconst. Surg.*, vol. 93, pp. 1035–40, "Improved Survival Rates of Random Flaps in Rabbits with a Monoclonal Antibody That Blocks Leukocyte Adherence," 1994.

ANGIOGENIC LIPID FORMULATIONS

CROSS REFERENCE TO RELATED APPLICATION

This patent application is a continuation-in-part of U.S. patent application Ser. No. 08/285,153 filed 3 Aug. 1994 and now abandoned.

TECHNICAL FIELD OF THE INVENTION

The present invention provides an angiogenic lipid formulation having an angiogenic lipid in an aqueous buffered vehicle. This formulation was surprisingly more effective than a typical "cream-like" formulation that would usually provide lipophillic therapeutic agents.

BACKGROUND OF THE INVENTION

A group of angiogenic lipid compounds were disclosed to have pharmacologic activity in stimulating angiogenesis, or promoting the directed growth of blood vessels. The genus of such angiogenic lipids was described in U.S. patent application Ser. No. 08/285,153 filed 3 Aug. 1994 and now abandoned, the disclosure of which is incorporated by reference herein. Angiogenesis is the process by which new blood vessels are formed and it is also know as neovascularization.

Tissue grafts are used in a variety of surgical reconstructions. Vascularization is critical to their success, as by definition, grafts have no blood supply of their own. Therefore, grafts are completely dependent on the recipient bed and adjacent tissues for revascularization. If the grafted tissue is too thick or the revascularization process inadequate, the graft will be either partially or entirely lost. Consequently, not only may the reconstructive result be jeopardized, but prolonged hospitalization, septic complications, and patient death may also occur.

Angiogenesis is a complex multi-step process regulated by a delicately balanced combination of both stimulatory and inhibitory factors (Folkman and Klagsburn, *Science* 235:442–447, 1987). These principally peptide factors have been isolated from various tissues and cell types within the body (Folkman and Klagsburn, *Science* 235:442–447, 1987; and Schultz and Grant, *Eye* 5:170–180, 1991). The omentum has been used to augment focal and localized blood delivery (DeRenzi and Boeri, *Berl. klin. Woch.* 40:773–775, 1903; and Wilkie, *Br. Med. J.* 2:1103–1106, 1911). Omental transposition can result in increased blood flow to specific vascularly compromised anatomic sites and tissues, and such surgical techniques have yielded successful revascularization of ischemic or otherwise hypovascular structures (Vineberg, *Dis. Chest* 54:315–322, 1968; and Goldsmith, *J. Neurosurg.* 66:152–153, 1987). In addition, the omentum is also believed to possess intrinsic angiogenic potential capable of initiating sustained tissue vascularization. Omental lipid extracts have demonstrated angiogenic properties in several experimental settings (Goldsmith et al., *Surg. Gyn. & Obs.* 162:579–583, 1986; and Nottebaert et al., *J. Orthop. Res.* 7:157–169, 1989).

It is believed that enhanced vascularization of tissue grafts can simultaneously result in increased clinical success and diminished graft failure-associated morbidity. Therefore there is a need in the art to improve vascularization of tissues, grafted tissues and ischemic tissue. The present invention provides surprising results for a formulation of lipid compounds that can be therapeutically effective for tissue vascularization and the surprising results showing that the type of formulation improves therapeutic effectiveness.

SUMMARY OF THE INVENTION

The present invention provides a locally-administered aqueous formulation for vascularizing ischemic or grafted tissue, comprising an alk-1-enyl glycerol derivative having a formula I or a formula II:

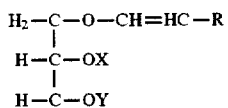

wherein R is a straight or branched $C_{1-24}$ alkyl or a straight or branched $C_{1-24}$ saturated or unsaturated alkyl and X and Y each is H or a saturated or unsaturated alkyl group having from 2 to 26 carbon atoms, or a monoglyceride having a $C_{8-24}$ ether-linked saturated alkyl in an aqueous buffered pharmaceutical carrier; or formula II

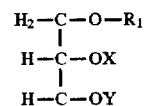

wherein X and Y are described in formula I and $R_1$ is a $C_{6-24}$ saturated or unsaturated alkyl. Preferably, R is $C_{14}$ or $C_{16}$ aryl, X is an aryl group and Y is H. Most preferably, R is a $C_{16}$ monounsaturated alkyl. Most preferably, $R_1$ is a $C_{18}$ saturated or unsaturated alkyl and X and Y are H. Preferably, the formulation further comprises an effective amount of an immunosuppressive compound. Examples of immunosuppressive compounds are cyclosporin A, cyclosporin G, mycophenolic acid malpholinoethylester, rapamycin, FK506, brequinar, misorabine, and glucocorticosteroids. Preferably, when the formulation includes a compound from formula II, the formulation further comprises a phosphotidylinositol as an emulsifier.

DETAILED DESCRIPTION OF THE INVENTION

Figure 1:
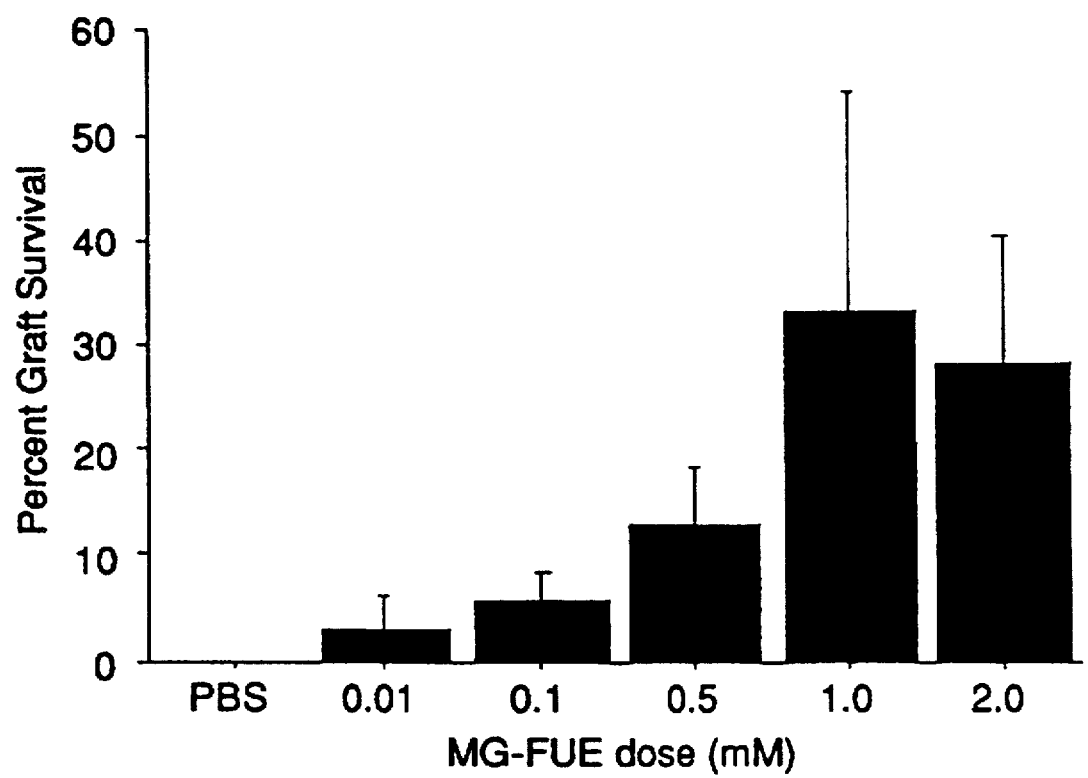
FIG. 1 illustrates a graph showing the percent full-thickness graft survival at 14 days engraftment treated with the preferred compound MG-FUE (monoglyceride fatty unsaturated ether having Y and X as H and R is predominantly a $C_{16}$ aryl monounsaturated) in phosphate buffered saline (PBS) aqueous formulation.

The semi-synthetic composition, MG-FUE, is composed primarily of an alk-1-enyl monoglyceride having a C18 aryl chain at the sn-1 position. This composition dramatically stimulated neovascularization in the rabbit cornea as a model of angiogenesis. The angiogenic potential of the lipid composition, monoglyceride-fatty unsaturated ether (MG-FUE), was studied in an accepted and reproducible rabbit composite graft (Vedder et al., *Plast. Reconst. Surg.* 93:1035–1040, 1994; and Hammond et al., *Plast. Reconstr. Surg.* 91:316–21, 1993) to further examine its effect on tissue vascularization. Therapeutic activity to enhance tissue vascularization depends upon the formulation used, Surprisingly, therapeutic activity requires an aqueous formulation rather than an oil-based emulsion that one would normally expect with a lipid-based active ingredient.

Synthesis of MG-FUE

Bovine heart phosphatidylcholine (30% plasmalogen), denoted as PC, was obtained either by purification, or directly from Sigma. One gram of PC was dissolved in 100 ml of chloroform and subjected to alkaline methanolysis by addition of 100 ml of 0.5 N methanolic NaOH (final was 0.25 N NaOH), gently mixed and allowed to react for 45 minutes at 25° C. The reaction was stopped by the addition of 50 ml of 1 N acetic acid. The reaction mixture was transferred to a 500 ml sepratory funnel, mixed and inverted and then allowed to partition over 1 hr. The lower phase containing the lipid was drawn off and dried using a roto-evaporator at room temperature or with slight warming to 37° C.

The resultant dried lipid, containing the lysoplasmenyl PC, LPPC, was brought up in 6.0 mls of 2-propanol:hexane:water (55:40:5) and applied to a preparative column (5×100 cm) packed with Iatrobeads® (Iatron, Tokyo), which are a porous silica gel of about 10 uM diameter. The column was first pre-equilibrated by running at 5.0 mils/min over 120 minutes using the gradient: 2-propanol:hexane:water (55:25:20) to (55:40:5). The column was washed for an additional 30 minutes at (55:40:5), and the sample applied in a 10 ml sample loop.

Fractions were collected over 400 minutes, 2 min/tube, hence 200 tubes. Elution was at a constant flow rate of 3.0 mls/min. Gradient elution was as follows: From T=0 min: 2-propanol:hexane:water (55:40:5) to T=300 min: (55:25:20) to T=400 min: (55:25:20). Purified LPPC eluted between fractions 72–96. These tubes were pooled, dried by roto-evaporation and brought up in a suitable volume of 6 uM Imidazole buffer, pH 7.4 with 2.2 mM $CaCl_2$. The lipid suspension was warmed, sonicated and vortexed. A suitable amount of Phospholipase C *Bacillus cereus* (Boehringer Mannheim) (10,000–50,000 units) was added and the reaction allowed to go until completion (greater than 12 hours). Finally, the resultant MG-FUE was purified from the reaction mixture by a similar HPLC protocol as above, but starting with more nonpolar conditions (e.g., 2-propanol:hexane:water, 35:64:1). The resultant purified MG-FUE was dried by roto-evaporator, brought up in a minimal volume of chloroform and stored at −20° C. over argon. Stored in this manner, there was no degradation over a 12 month period.

Compound Genus

The compound genus of the present inventive aqueous formulation for vascularizing ischemic or grafted tissue, comprises an alk-1-enyl glycerol derivative having a formula I or a formula II:

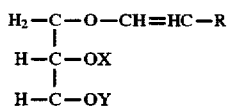

wherein R is a straight or branched $C_{1-24}$ alkyl or a straight or branched $C_{1-24}$ saturated or unsaturated alkyl and X and Y each is H or an a saturated or unsaturated alkyl group having from 2 to 26 carbon atoms, or a monoglyceride having a $C_{8-24}$ ether-linked saturated alkyl in an aqueous buffered pharmaceutical carrier, or formula II

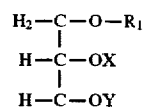

wherein X and Y are described in formula I and $R_1$ is a $C_{6-24}$ saturated or unsaturated alkyl. Preferably, R is $C_{14}$ or $C_{16}$ saturated or unsaturated alkyl, X is an aryl group and Y is H. Most preferably, R is a $C_{16}$ monounsaturated aryl. Most preferably, $R_1$ is a $C_{18}$ saturated or unsaturated alkyl and X and Y are H. Preferably the formulation further comprises an effective amount of an immunosuppressive compound. Examples of immunosuppressive compounds are cyclosporin A, cyclosporin G, mycophenolic acid malpholinoethylester, rapamycin, FK506, brequinar, misorabine, and glucocorticosteroids. The preferred embodiment is MG-FUE, which consists of X and Y as a hydrogen and R is $C_{16}$ monounsaturated alkyl. Alternatively, X is an acyl group and Y is H or vica versa, wherein said acyl group comprises 20 carbon atoms (e.g., an arachidonate group). Preferably, X is an acyl group comprising 16 or 18 carbon atoms.

In Vivo Experiments

A series of experiments were performed using anesthetized New Zealand white rabbits having free dorsal composite grafts consisting of skin, subcutaneous tissue, and the panniculus carnosus muscle elevated and removed and the deep surfaces of the grafts coated with varying doses (N=4-8 per dose) of MG-FUE suspended in phosphate-buffered saline aqueous formulation (PBS), or additionally having 1.8% calcium alginate in an emulsified cream formulation (Unibase® Warner Chilcott, Morris Plains N.J., composed of cetyl alcohol, stearyl alcohol, white petrolatum, glycerin, sodium lauryl sulfate and propyl paraben). The control rabbits were treated with vehicle alone (N=14). Grafts were sutured in position and assessed daily for 14 days. Graft viability was quantified as the surface area of clearly viable dermis and expressed as a percentage of total graft surface area. Samples of all grafts were sectioned, prepared with H&E stains, and examined histologically. Areas of full-thickness tissue revascularization were seen at all treatment doses, whereas dermal viability was completely absent in controls. The percentage of viable dermal surface area varied in a dose-dependent fashion (FIG. 1). There was a significant (*$p<0.05$) increase in tissue viability in grafts treated with either 1.0 mM or 2.0 mM MG-FUE compared to grafts treated with either a lower dose or PBS alone. Examined histologic sections demonstrated successful graft revascularization in the MG-FUE-treated grafts but only partial thickness revascularization of the deeper muscle layers in controls. There was observed a dose-dependent angiogenic effect of the genus of lipid compounds that resulted in enhanced graft revascularization and a significant improvement in full-thickness tissue viability. These data serve as a predictive model for improving tissue vascularization and particularly ischemic tissue vascularization. The effect of MG-FUE was dose-dependent. Moreover, only the aqueous formulation provided statistically significant results, whereas the same doses in the alginate/cream formulation failed to achieve statistical significance.

Tissue grafts have no intrinsic blood supply. Tissue grafts are entirely dependent on the recipient bed and adjacent tissues for revascularization. Unless revascularization occurs prior to cell death, the graft will fail. When the coated grafts were elevated and returned to their positions, an interface between the recipient beds and surrounding tissues was created. Consequently recipient beds are directly exposed to the study compound and, are treated by it just as the grafts are. This technique of topical lipid compound application to the deep surface of the graft created a localized microenvironment impregnated with compound or placebo vehicle control.

The enhanced tissue vascularization and significantly improved graft viability demonstrated in the illustrated in vivo study was due solely to MG-FUE, which result was greatly improved when an aqueous formulation was used instead of the alginate/unibase formulation. Full-thickness tissue viability was identified at all MG-FUE doses. No dermal viability was detected in control grafts. All such control grafts suffered late slough implying prolonged ischemia and necrosis of all tissue components, due to failure of timely revascularization. The preferred lipid compound, monoglyceride-fatty unsaturated ether (MG-FUE) when in an aqueous formulation and not an emulsified cream formulation, enhanced tissue vascularization and significantly improved composite graft tissue full-thickness viability in this in vivo predictive model. In the clinical setting, such an approach will improve tissue graft survival and reduce associated morbidity. Moreover, the addition of an emulsifying agent to the formulation, such as phosphotidylinositol (FIG. 2) did not block the angiogenic properties of MG-FUE and may be needed to solubilize other angiogenic lipids into an aqueous-based formulation.

EXAMPLE 1

This example illustrates a set of experiments that saw a dose-response relationship for improving tissue vascularization for the compound MG-FUE. Preparations of study compound, MG-FUE were suspended in two different formulations.

In the initial phase of this study, sterile MG-FUE was mixed with sterile, filtered 1.8% alginate dissolved in phosphate-buffered saline (PBS), pH 7.4, without $Ca^{++}$ or $Mg^{++}$. An equivalent volume of sterile Unibase® was added to this, and the formulation was then sonicated for 1 minute and vortexed for 30 seconds. The compound was diluted to final concentrations of 0.66 and 6.66 mM. These preparations were stored in glass vials at 4° C. until use.

Sterile MG-FUE was suspended in sterile phosphate-buffered saline (PBS). MG-FUE was diluted to final concentrations of 0.01, 0.1, 0.5, 1.0 and 2.0 mM in PBS. The compound was stored in sterile glass vials at room temperature. Approximately one hour before application, MG-FUE was heated to 37° C. in an agitating water bath to promote maximal dissolution. Immediately before application, the heated samples were vigorously vortexed for 2 min. to ensure complete mixing.

New Zealand white rabbits (1.5-2 kg) were used for this study. They were maintained under approved standard laboratory animal conditions with appropriate veterinary care. Access to a standard diet of food and water ad libitum was maintained.

The experimental method and surgical procedures of this study were performed in accordance with established N.I.H. guidelines for animal experimentation and with formal approval of the University of Washington Animal Care Committee. Rabbits were anesthetized with an intramuscular dose of ketamine (30 mg/kg) and xylazine (2 mg/kg). A lower extremity peripheral heparin-lock and IV were placed. A single intravenous dose of cefazolin (25 mg/kg) was administered, and a titratable intravenous anesthetic preparation was secured. The entire dorsum of the rabbit extending from the scapular tip to the posterior iliac crest was shaved and a sterile prep with Betadine® solution was performed. Excess solution was removed with normal saline. The rabbit was then draped for sterile surgery.

A gridded template was used to mark two 4×4 cm grafts. Attempts were made to maintain an intact tissue bridge of >2 cm between the grafts. A circumferential full-thickness skin incision was made around the template and carried through the subcutaneous tissue. The underlying panniculus carnosus muscle was similarly incised and sharply divided with scissors. Complete dissection of the deep a vascular connective tissues allowed each graft to be fully elevated and removed. Both graft and recipient bed kept from desiccating by wrapping the grafts in saline-moistened gauze and placing them directly onto the recipient bed. The tissues were maintained at room temperature.

MG-FUE was removed from the 37° C. water bath, vigorously vortexed for 2 min., and 1.0 ml aspirated with a 19-gauge needle. Grafts were unwrapped, and 0.5 ml aliquots of compound were then directly applied to the deep surface of each. Control grafts were treated with equivalent volumes of PBS in an identical fashion. The grafts were anatomically oriented and repositioned, allowing the MG-FUE or PBS control to directly contact the recipient bed as well. The grafts were then sutured into place with 4-0 silk suture in running fashion. The operative wounds were gently cleansed. No dressings were applied. A treatment dose identification card was made and immediate post-operative photography was performed. The IV and heparin lock were discontinued and hemostasis assured. The rabbit was then returned to the vivarium where it was allowed to recover. An initial post-operative check to ensure the rabbit's well-being took place ~30 min after completion of the procedure.

Rabbits and grafts were assessed daily for a 2-week post-operative period. During this period, the surface areas of all grafts were repeatedly calculated, and grafts examined for the presence of hematoma, seroma, dehiscence or slough. Seromas were aspirated. All grafts were measured and photographed on days 1 and 14 and intermittently in-between. Graft viability was determined by visual inspection and included assessments of tissue color, capillary refill, bleeding upon needle puncture, and the presence or absence of dermal eschar. Tissue texture was evaluated by direct palpation. Findings were recorded and graft size-matched templates were correspondingly marked to demonstrate progressive eschar or other color change. Final clinical graft viability was quantified on day #14. Using a transparent gridded template, both the total graft size and regions of clinically viable dermis were measured. Graft viability was quantified as the surface area of clearly viable dermis and expressed as a percentage of total graft surface area. Mean percentage graft survival for each treatment was calculated and a dose-response curve plotting percentage graft survival vs. MG-FUE dose was derived. Dose-dependent differences in percentage graft survival were calculated using the unpaired t-test with significance determined at a p-value of <0.05.

At the conclusion of the post-operative study period, rabbits were euthanized with an intraperitoneal dose of sodium pentothal. The entire dorsal composite panel including both grafts and surrounding skin, subcutaneous tissue, and panniculus carnosus muscle was meticulously dissected in the avascular plane deep to the muscle. Both the undersides of the grafts and their respective recipient beds were clinically assessed for the presence of neovascularization and photographed. Grafts were transversely incised, and full-thickness tissue evaluations for evidence of bleeding indicative of successful revascularization were performed.

Samples of all grafts were collected, labeled according to graft site, MG-FUE dose and vehicle, and placed in 10% neutral-buffered formalin. Each was submitted for H&E staining and histologic evaluation for the presence and anatomic localization of newly formed vascular structures. Two rabbits had two grafts apiece treated with either 0.01, 0. 1, 0.5, or 1.0 mM MG-FUE. Five rabbits had two grafts treated with 2.0 mM MG-FUE in PBS. There were seven PBS control rabbits.

Results

The results of this experiment were reviewed in phases based upon vehicle utilized. Four rabbits had two 3×4 cm composite grafts elevated and treated with 6.66 mM MG-FUE suspended in an alginate/Unibase vehicle and another four had two equivalent sized grafts treated with 0.66 mM MG-FUE in the same vehicle. No viable dermis, regardless of MG-FUE dose, was detected at the end of the study period. Three of eight grafts treated with both low-dose MG-FUE and vehicle alone partially sloughed during the second post-operative week and were not considered suitable for data interpretation. During the first post-operative week, MG-FUE-treated grafts manifested a pale color and a boggy, edematous tissue quality. Capillary refill was not present and there was no bleeding with a needle puncture. Rather than blood, persistent liquid-state vehicle was identified. All grafts underwent progressive necrosis, and post-mortem examination confirmed that all had been completely replaced by full-thickness eschar. Meticulous dissection revealed the presence of viscous desiccated Unibase/alginate vehicle that had become sequestered immediately deep to the panniculus carnosus muscle of each graft. Although all tissues superficial to the loculated vehicle were nonviable, macroscopic evidence of new vessel formation was present on several of the graft recipient beds. Radially oriented vascular structures, specifically limited to the area representing the graft-recipient bed interface, were evident. Their origins appeared to be from deep within the recipient bed. These finding were exclusively limited to MG-FUE-treated grafts only and were more prominent under those treated with the lower dose. Clinically detectable neovascularization was not present under those grafts treated with alginate/Unibase® vehicle alone.

Areas of full-thickness tissue vascularization were noted at all treatment doses. Dermal viability was absent in PBS control-treated grafts. For those treated with MG-FUE, the percentage of viable dermal surface area varied in a dose-dependent fashion (FIG. 1). There was a significant ($p<0.05$) increase in tissue viability in grafts treated with either 1.0 mM or 2.0 mM MG-FUE compared to grafts treated with either a lower dose of MG-FUE or PBS alone.

Noteworthy complications (see table below) include one 2.0 mM-treated day 3 rabbit death, two 0.01 mM (PBS)-treated day 10 episodes of graft epidermolysis, one 0.1 mM (PBS) day 3 and one 0.5 mM (PBS)-treated day 7 graft dehiscence, and three PBS control full-thickness graft sloughs during the second week of the 2-week assessment period. All complicated grafts were eliminated from data analysis.

| Dose (mM) | Rabbit N | Graft N | complication | # @ risk grafts | # plotted grafts |
|---|---|---|---|---|---|
| 0.01/alginate | 2 | 4 | none | 0 | 4 |
| 0.1/PBS | 2 | 4 | none | 0 | 4 |
| 0.1/alginate | 2 | 4 | dehiscence | 1 | 3 |
| 0.5/PBS | 2 | 4 | dehiscence | 1 | 3 |
| 0.5/alginate | 2 | 4 | none | 0 | 4 |
| 1.0/PBS | 2 | 4 | none | 0 | 4 |
| 1.0/alginate | 2 | 4 | none | 0 | 4 |
| 2.0/PBS | 5 | 10 | rabbit death | 2 | 8 |
| alginate | 2 | 4 | none | 3 | 11 |
| PBS | 7 | 14 | slough | 3 | 11 |

The majority of grafts remained soft and pale during the early period of clinical observation. Most of these treated grafts progressed to take on a dusky gray/purple hue with viable portions subsequently becoming pink. Convincing evidence of partial graft loss did not manifest until approximately the fifth to seventh post-operative day at which time focal areas of eschar were prominent. Simultaneous to the development discrete eschar, many remaining portions were pink, soft and had brisk capillary refill. Healthy portions of the grafts bled when challenged with needle punctures.

Post-mortem examination of the graft undersurfaces revealed many moderately large-caliber vessels embedded within the deep tissues of the grafts. These new vessels appeared to have their origins within the tissues peripheral to the suture lines. Elevation of the 1.0 mM treated (both PBS and alginate) graft tissues revealed long large-caliber vessels coursing upward from the recipient beds, penetrating the deep surface of the grafts. Full-thickness areas of tissue viability were identified in all MG-FUE-treated. Dermal viability was completely absent in controls. Non-viable tissue was clearly demarcated by the presence of dark, dry, hard eschar. Viable tissue was thick, edematous and pink. Grafts were sectioned transversely and upon direct compression, blood emanated from the those portions that had been successfully revascularized. Sections demonstrate successful graft revascularization in the MG-FUE-treated grafts but only partial thickness revascularization of the deeper muscle layers in controls.

The enhanced tissue vascularization and significantly improved graft viability demonstrated in this experiment was due solely to the study compound MG-FUE. Full-thickness tissue viability was identified at all MG-FUE doses when suspended in PBS. No dermal viability was detected in PBS-coated control grafts, and all such control grafts suffered late slough implying prolonged ischemia and necrosis of all tissue components, due to failure of timely revascularization. Despite the finding of a single partially vascularized calcium-alginate control graft, use of this vehicle did not significantly augment tissue vascularization and graft viability.

These data also demonstrated that in order to clinically express the angiogenic capacity of MG-FUE, selection of a proper soluble aqueous vehicle is critical. Post-mortem evaluation of the undersurfaces of grafts treated with MG-FUE suspended in a Unibase-containing vehicle revealed that tremendous neovascular networks had developed on the recipient bed surfaces. However, immediately superficial to these newly formed vessels viscous desiccated vehicle remained loculated and sequestered. It is possible that the aggregate vehicle acted as a physically impermeable barrier and impeded the growth of new blood vessels into the grafts. Tissue vascularization, therefore, failed and all grafts become necrotic. It did, however, concentrate the MG-FUE at the recipient bed, leading to an intense neovascularization response within the tissue bed. This effect was eliminated when we selected PBS or 1.8% calcium-alginate alone to serve as vehicles. Grafts were successfully vascularized, and post-mortem examination was remarkable not only for the lack of sequestered vehicle, but also for demonstration of new vessels migrating directly into the deep surfaces of treated grafts.

EXAMPLE 2

This example illustrates a second experiment (FIG. 2) in which 2 mM phosphotidylinositol (PI) was used to solubilize the angiogenic lipid into an aqueous PBS vehicle. The three angiogenic lipids tested were 2 mM MG-FUE, 2 mM monoglyceride ether (18:1) ("ether") and 2 mM monoacylglycerol (18:2) ("MAG" Nucheck). Each of the angiogenic lipids were evaporated to dryness by nitrogen in sterile glass tubes and brought up to a final volume of 80 µl ethanol, sonicated, added 200 µl sterile water, sonicated, added 3.72 ml sterile PBS (without calcium or magnesium), warmed and sonicated. The solutions were without precipitate and slightly cloudy in appearance.

Figure 2:
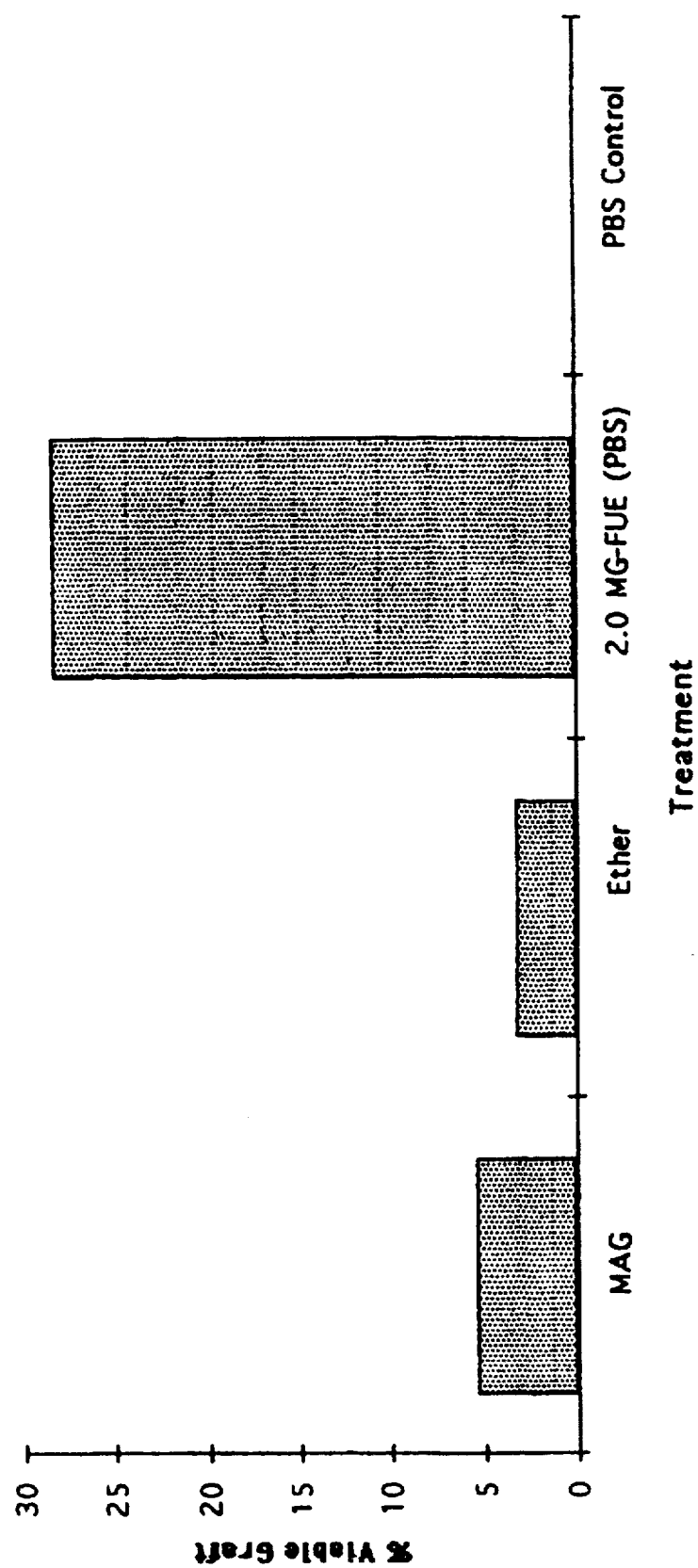
FIG. 2 illustrates a comparison for graft tissue viability comparing MG-FUE to monoacylglycerol (18:2) ("MAG"), and monoglyceride ether (18:1) ("ether"), along with PBS control vehicle. Each vehicle was supplemented with 2 mM phosphatidylinositol emulsifier to help solubilize especially the MAG and ether formulations. At the day 14 observation point shown, the MG-FUE treatment exhibited the greatest percentage viable graft tissue.

The skin graft experiment, as described in example 1, was performed for each of the three angiogenic lipid samples (each at 2 mM concentration), along with a PI and PBS vehicle control. As shown in FIG. 2, all three angiogenic lipids exhibited greater angiogenic and tissue vascularization effect than the control. However, the effect of MG-FUE was far greater than the other two lipids. Measurement of grafted tissue viability was taken at the standard 14 day post graft time period.

I claim:

1. An aqueous formulation for vascularizing ischemic or grafted tissue, comprising a glycerol derivative having the following formula:

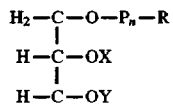

wherein R is a straight or branched $C_{1-24}$ saturated or unsaturated alkyl or a straight or branched $C_{1-24}$ aryl; $P_n$ is —CH=HC—; n is 0 to 1, with the proviso that when n is 0, R is $C_{6-24}$, and X and Y are each independently H or an aryl or alkyl group having from 2 to 26 carbon atoms, or a monoglyceride having a $C_{8-24}$ ether-linked saturated alkyl in an aqueous buffered pharmaceutical carrier.

2. The aqueous formulation of claim 1 wherein R is $C_{14}$ or $C_{16}$ saturated or unsaturated alkyl, X is a saturated or unsaturated alkyl group and Y is H.

3. The aqueous formulation of claim 1 R is a $C_{16}$ monounsaturated alkyl.

4. The aqueous formulation of claim 1 wherein the compound further comprises an immunosuppressively effective amount of an immunosuppressive compound.

5. The aqueous formulation of claim 4 wherein the immunosuppressive compound is selected from a group consisting of cyclosporin A, cyclosporin G, mycophenolic acid malpholinoethylester, rapamycin, FK506, brequinar, and glucocorticosteroids.

6. The aqueous formulation of claim 1 wherein the aqueous formulation further comprises an emulsifying concentration of phosphotidylinositol.

7. The aqueous formulation of claim 6 wherein the concentration of phosphotidylinositol is from about 0.5 mM to about 10 Mm.

8. An aqueous formulation of claim 1 wherein X and Y are both hydrogen, n is 1 and R is $C_{16}$ aryl.

9. An aqueous formulation of claim 8 further comprising an emulsifying agent.

10. The aqueous formulation of claim 4 wherein R is a $C_{18}$ alkyl and n is 0.

* * * * *